(12) United States Patent
Gunnes et al.

(10) Patent No.: US 8,981,055 B2
(45) Date of Patent: Mar. 17, 2015

(54) METHODS FOR MANUFACTURING AN ANTIFUNGAL AGENT

(75) Inventors: Solvi Gunnes, Lommedalen (NO); Harald Halvorsen, Oslo (NO)

(73) Assignee: Xellia Pharmaceuticals APS (DK)

( * ) Notice: Subject to any disclaimer, the term of this patent is extended or adjusted under 35 U.S.C. 154(b) by 8 days.

(21) Appl. No.: 14/009,462

(22) PCT Filed: Mar. 26, 2012

(86) PCT No.: PCT/EP2012/055284
§ 371 (c)(1),
(2), (4) Date: Nov. 4, 2013

(87) PCT Pub. No.: WO2012/136498
PCT Pub. Date: Oct. 11, 2012

(65) Prior Publication Data
US 2014/0371422 A1     Dec. 18, 2014

Related U.S. Application Data

(60) Provisional application No. 61/471,218, filed on Apr. 4, 2011.

(51) Int. Cl.
*A61K 38/00* (2006.01)
*A61K 38/08* (2006.01)

(52) U.S. Cl.
CPC ..................... *A61K 38/08* (2013.01)
USPC ........................................................ 530/333

(58) Field of Classification Search
None
See application file for complete search history.

(56) References Cited

U.S. PATENT DOCUMENTS 6,107,458 A     8/2000     Ohki et al.
7,199,248 B2    4/2007     Tsuboi et al.

OTHER PUBLICATIONS

FK-463 "Antifungal" in Drugs of the Future; 23(12); pp. 1273-1278; (1998).
Valeur et al.; "Amide Bond Formation: Beyond the Myth of Coupling Reagents"; Chem. Soc. Rev., 38; pp. 606-631; (2009).
Hashimoto, Seiji; "Micafungin: a Sulfated Echinocandin"; The Journal of Antibiotics; 62; pp. 27-35; (2009).
Joullie et al.; "Evolution of Amide Bond Formation"; ARKIVOC (ARKAT USA, Inc.); (viii); pp. 189-250; (2010).
Ohigashi et al.; "Process Development of Micafungin, a Novel Lipopeptide Antifungal Agent"; Journal of Synthetic Organic Chemistry, Japan; 64(12); pp. 1294-1303; (2006); with English abstract.
Ohigashi et al.; "Practical Synthesis of FR195752, the Side Chain of Micafungin, Utilizing a Reyloselective Conversion of Diaryl-Beta-diketone to 3,5-Diarylisoxazole"; Organic Process Research & Development 9; pp. 179-184; (2005).
Subiros-Funosas et al.; "Oxyma: An Efficient Additive for Peptide Synthesis to Replace the Benzotriazole-Based HOBt and HOAt with a Lower Risk of Explosion"; Chem. Eur J. 15(37); pp. 9394-9403; (2009).
International Search Report and Written Opinion; International Application No. PCT/EP2012/055284; International Filing Date Mar. 26, 2012; Date of Mailing May 15, 2012; 11 pages.
Pu et al.; "A Practical Method for Functionalized Peptide or Amide Bond Formation in Aqueous-Ethanol Media with EDC as Activator"; Organic Process Research & Development; 13; pp. 310-314; (2009).

*Primary Examiner* — Thomas S Heard
(74) *Attorney, Agent, or Firm* — Cantor Colburn LLP (57) ABSTRACT

The present invention relates to an improved process for the preparation of Micafungin.

14 Claims, 4 Drawing Sheets

METHODS FOR MANUFACTURING AN ANTIFUNGAL AGENT

CROSS-REFERENCE TO RELATED APPLICATIONS

This application is a 371 of PCT/EP2012/055284 filed Mar. 26, 2012, which claims the benefit of priority to U.S. provisional application No. 61/471,218 filed on Apr. 4, 2011, under the provisions of 35 U.S.C. 119 and the International Convention for the protection of Industrial Property, which are incorporated herein by reference.

FIELD OF INVENTION

The present invention relates to an improved process for the preparation of Micafungin or salts thereof.

STATE OF THE ART

Micafungin is an echinocandin with antifungal activity represented by formula (I):

(I)

Micafungin is also known as Pneumocandin A0, 1-[R4R,5R)-4,5-dihydroxy-N2-[4-[5-[4-(pentyloxy)phenyl]-3-isoxazolyl]benzoyl]-L-ornithine]-4-[(4S)-4-hydroxy-4-[4-hydroxy-3-(sulfooxy)phenyl]-L-threonine]. Micafungin sodium is furthermore known as FK-463. The assigned Registry No's by Chemical Abstracts are 235114-32-6 for Micafungin and 208538-73-2 for Micafungin sodium.

The antifungal activity of Micafungin is due to its ability to inhibit 1,3-β-D-glucan synthase and thus leads to fungal cell lysis. Micafungin is thus useful in the treatment of various infections; inter alia infections caused by strains of e.g. *Aspergillus, Cryptococcus, Candida, Mucor, Actinomyces, Histoplasma, Dermatophyte, Malassezia* and *Fusarium*. Micafungin is the active ingredient in the approved drugs Mycamine® and Funguard® which are used in the treatment and prophylaxis of infections caused by *Candida*.

Micafungin is the second approved antifungal agent in the echinocandin series and is now used world wide in chemotherapy for life-threatening fungal infections.

Micafungin and the preparation thereof is disclosed in the U.S. Pat. No. 6,107,458 issued to Fujisawa Pharmaceutical Co., Ltd. A method for preparing Micafungin is also disclosed in the General Thesis, "Process Development of Micafungin, a Novel Lipopeptide Antifungal Agent" by Ohigashi et al. in Journal of Synthetic Organic Chemistry, Japan, vol. 64, No. 12, December 2006. According to the methods disclosed in the prior art, Micafungin may be obtained via FR-901379, a natural product isolated from the fungus *Coleophoma empetri* F-11899. By enzymatic deacylation of FR-901379, followed by amide coupling of 4-[5-(4-pentyloxy)phenyl) isoxazole-3-yl]benzoic acid, Micafungin can be produced.

A method for preparing Micafungin is also disclosed in Fromtling et al., supra. The peptide core obtained after deacylation of FR-901379 is according to Fromtling et al. reacylated with an activated side chain, 1-[4-[5-(4-pentyloxy)phenyl)isoxazol-3-yl]benzoyl]benzotriazole 3-oxide.

Various methods for manufacture of Micafungin sodium are also disclosed in Hashimoto et al., *The Journal of Antibiotics* (2009) 62, 27-35.

An improved production of Micafungin is described in U.S. Pat. No. 7,199,248. This method also comprises a step of adding the isolated Micafungin side chain, i.e. 1-[4-[5-(4-pentyloxy)phenyl)isoxazol-3-yl]benzoyloxy]-1H-1,2,3-benzotriazole to the deacylated Micafungin peptide core.

Ohigashi et al, Organic Process Research & Development, 2005, vol. 9, page 179-184, disclosed an optimized industrial Micafungin production process which also involved isolating the activated Micafungin side chain.

For all the methods for preparing Micafungin disclosed in the prior art as referred to above, it is a common feature that all the known methods presuppose the separation of the activated Micafungin side chain prior to the reaction with the Micafungin peptide core, i.e. FR-901379. Thus, all the prior art processes proceed via an isolated form of the activated Micafungin side chain.

It is an object of the present invention to provide an improved and more industrially efficient method for preparing Micafungin.

SUMMARY OF THE INVENTION

The object of the present invention is according to one aspect achieved by using a process that involves activation of Micafungin side chain and the coupling of said Micafungin side chain to the Micafungin peptide core in a one-pot procedure. That is, the process of the present invention involves acylation of the Micafungin peptide core without isolating the activated Micafungin side chain from its pertaining reaction mixture. In another aspect, the invention involves activation and coupling of the Micafungin side chain to the Micafungin core peptide in one reaction mixture. Thus, a method is provided wherein the step of isolating the activated Micafungin side chain is superfluous.

The coupling of an acidic compound as the Micafungin side chain to a peptide core, as the Micafungin core, may result in various unwanted by-products. Reference is inter alia made to Ohigashi et al, 2006, supra, inter alia discussing the need for suppression of the side reactions in the acylation reaction due to the presence of a multitude of functional groups in the Micafungin core. Ohigashi et al. 2006 furthermore teach that there is a need for optimal purification conditions for the intermediates of the process. Despite the teaching of the prior art, the present inventors have surprisingly discovered that the coupling of the Micafungin side chain may be activated and coupled directly to the Micafungin core without the need for a separate separation step isolating the activated Micafungin side chain and wherein successful coupling with minimal impurity generation was achieved. The method of the present invention provides advantages compared with the prior art method presupposing separation of the activated Micafungin side chain. For example, a one-pot process is more efficient from an industrial point of view in respect of shorter process time due to the omitting of an isolation step. In addition, with better utilization of the activated Micafungin side chain, no product will be lost due to an isolation/purification step resulting in an overall better yield.

More specifically, the present invention provides a one-pot process for the manufacturing of Micafungin or a salt thereof comprising the following order of steps:

a) mixing a compound of the formula (III)

(III)

or a salt thereof, and a coupling additive selected from the group consisting of hydroxybenzotriazols and ethyl-2-cyano-2-(hydroxyimino)acetate in a solvent;

b) adding an coupling reagent to the mixture obtained in step a), wherein said coupling reagent is a carbodiimide;

c) adding a base and a compound of formula (II)

(II)

or a salt thereof to the mixture obtained in step b)

According to one embodiment of the present invention, the coupling additive is 1-hydroxy-benzotriazole.

According to another embodiment of the invention, the coupling additive is 1-hydroxy-7-azabenzotriazole According to yet an embodiment of the invention, the coupling additive is ethyl-2-cyano(hydroxyimino)acetate.

According to another embodiment of the invention, the coupling reagent is 1-ethyl-3-(3-dimethylaminopropyl)carbodiimide (EDC) or a salt thereof, preferably the hydrochloride salt of EDC.

According to another embodiment of the invention, the solvent used in step a) above is DMF.

According to yet another embodiment of the invention, the base used in step c) of the present invention is DIPEA.

According to yet another embodiment of the invention, the base is added to the mixture obtained in step b) before adding the compound of formula II.

According to yet another embodiment of the invention, the base is added to the mixture obtained in step b) after adding the compound of formula II.

According to still another embodiment of the invention, the Micafungin salt obtained in step c) is precipitated.

According to still another embodiment of the invention, the Micafungin salt obtained in step c) is precipitated by using an antisolvent.

According to still another embodiment of the invention, the Micafungin salt obtained in step c) is precipitated by ethyl acetate.

According to yet another embodiment of the invention, the Micafungin salt obtained in step c) is precipitated after quenching of the reaction by addition of methanol and acetone.

DETAILED DESCRIPTION OF THE INVENTION

According to the present invention, Micafungin is any compound comprising the structure (I)

or salts thereof. The expression "salts thereof" is meant to embrace any salts of Micafungin that may be useful for the purpose of preparation and/or purification of Micafungin or any pharmaceutically acceptable salts of Micafungin useful as an active ingredient in a medicinal formulation. In this respect, a non-limiting list of salts of Micafungin is the sodium salt, the potassium salt, the diisopropylethylamine (DIPEA) salt, etc.

According to the present invention, Micafungin is prepared in one-pot by firstly a) mixing of the Micafungin side chain with an coupling additive, b) then adding a coupling reagent to the mixture of step a), and c) finally adding to this mixture a base and a compound of formula II as depicted above, i.e. the Micafungin peptide core.

The Micafungin side chain in acidic form is the compound with the chemical name 4-[5-(4-pentyloxy)phenyl]isoxazole-3-yl]benzoic acid. The Registry Number assigned by Chemical abstracts is 179162-55-1 and the name assigned by Fujisawa is FR-195752. This compound, which herein is also referred to as the Micafungin side chain, in acidic form, can be represented by the formula III (III)

The Micafungin peptide core is represented by the formula II.

(II)

The term "Micafungin peptide core" as used herein, is meant to also embrace salts of the compound of formula II. E.g. the sodium salt of the compound above is also known as FR-179642 (Fromtling et al. in Drugs of the Future, 1998, Vol 23, No 12, page 1273-1278).

In Micafungin, the Micafungin side chain is coupled to the Micafungin peptide core by an amide bond. Various methods for formation of amide bonds, that is the reaction of a carboxylic acid and an amine, are disclosed in the prior art and are used in the synthesis of peptides. For the most, the formation of an amide bond requires the use of activation of the carboxylic acid using a coupling reagent and coupling additive, c.f. Madeleine M. Joullie and Kenneth M. Lassen, in Arkivoc, 2010 (viii), 189-250 and Eric Valeur and Mark Bradley, 2009, Chem. Soc. Rev., 38, 606-631. There is also examples where quite simple peptide structures are prepared by amide bond formation in a one-pot procedure, cf. Pu et al., 2009, Organic Process Research & Development, 13, 321-314 wherein a method for the preparation of peptides in an aqueous ethanol mixture.

However, nowhere in the prior art is an one-pot procedure for the coupling of an carboxylic acid to an amine group of a complex molecule such as the Micafungin peptide core suggested.

As used herein, the term "Micafungin peptide core" or "Micafungin core" is the compound resulting from enzymatic deacylation of the palmitoyl moiety from FR-901379, represented by formula II depicted above. Fujisawa assigned the name FR-179642 for the Micafungin peptide core and the name FR-133303 for the sodium salt of the Micafungin peptide core. The assigned Registry No's for this compound by Chemical Abstracts is 168110-44-9. As used herein, the Micafungin peptide core is meant to embrace this compound as well as salts of this compound, e.g. the sodium salt FR-133303.

The first step of the one-pot method according to the present invention is the mixing of the Micafungin side chain and a coupling additive. After said mixing, a coupling reagent is added to the mixture resulting in the activation of the Micafungin side chain and the reaction with the reaction additive.

The term "coupling additive" as used herein represents any compounds that enhances the reactivity of the activated Micafungin side chain and facilitates the coupling to the primary amine of the Micafungin peptide core. The advantage of using a coupling additive is that it reduces the formation of by-products.

A vast array of coupling additives exists (see Chem. Soc. Rev., 2009, vol 38, page 606-631 by Valeur and Bradley). The term hydroxybenzotriazols is meant to embrace the hydroxybenzotriazoles, hydroxyazabenzotriazols and substituted derivatives thereof. E.g 1-hydroxybenzotriazole, 1-hydroxy-7-azabenzotriazole, 6-chloro-1-hydroxybenzotriazole etc.

According to the method of the present invention, 1-hydroxybenzotriazole (HOBt) and ethyl 2-cyano-2-(hydroxyimino)acetate (Oxyma Pure®, CAS no 3849-21-6, hereinafter Oxyma) have shown to be useful. The use of said coupling additives results in low impurity formation and high yields of the desired Micafungin.

The term "coupling reagents" as used according to the present invention is any compound capable of activating the carboxylic acid of the Micafungin side chain, in the presence of the coupling additive, and thereby facilitate its reaction with the amine of the Micafungin core structure.

As a coupling reagent according to the present invention, a carbodiimide derivative, represented by the following formula: Ra—N=C=N—Rb wherein Ra and Rb are the same or different, and each independently represent an aliphatic, heteroaliphatic, carbocyclic or a heterocyclic group, all said groups are optionally substituted, may be used. According to one aspect of the present invention, 1-ethyl-3-(3-dimethylaminopropyl)carbodiimide (EDC) is used as a coupling reagent. According to a preferred aspect of the present method, the hydrochloride salt of EDC is used as a coupling reagent.

It is known in the prior art that carbodiimides may be used as coupling reagents, see e.g. Valeur and Bradley, Chem. Soc. Rev June 2008. The negatively charged oxygen of the Micafungin side chain will ideally act as a nucleophile, attacking the central carbon of the diimide groups. The method of the present invention is illustrated below using Oxyma as a coupling additive and EDC as a coupling reagent, see scheme 1.

Suitable solvents for the one-pot reaction comprise polar aprotic organic solvents. A non-limiting list of suitable solvents includes dimethylformamide (DMF), dimethylacetamide (DMA), dimethylsulfoxide (DMSO) etc and mixtures thereof.

Suitable bases for the one-pot reaction comprise organic or inorganic bases able to protonate the amine group on the Micafungin peptide core. A non-limiting list of suitable bases includes DIPEA, $NaHCO_3$, $Na_2CO_3$ etc.

Suitable temperatures for the activation of the Micafungin side chain are from 0° C. to 40° C., preferably at 20° C.-30° C.

Suitable temperatures for the coupling of the Micafungin side chain to the Micafungin peptide core is −5° C. to 10° C., preferably at 0° C. It is also preferred to achieve said temperature before addition of the base.

Suitable total reaction time for the one-pot procedure is from about 4 h to 20 h. Preferably, 2-4 h for the activation of the Micafungin side chain, and 90 min to 2 h for the coupling of the activated Micafungin to the Micafungin peptide core.

It is important that the coupling reagent is added after the mixing of the coupling additive and the Micafungin side chain.

The reaction scheme 1 below illustrate the activation of the Micafungin side chain and reaction of the activated Micafungin side chain with the Micafungin peptide core happening in the one-pot process of the present invention.

Reaction scheme 1:

After the coupling of the Micafungin side chain to the Micafungin peptide core, the product thereof may be precipitated as a salt of Micafungin. The term "Micafungin salt" may in this respect be any pharmaceutically active salt or a salt useful for further purification of Micafungin. In the latter case, the salt of Micafungin may for example be the N,N-diisopropyl ethylamine (DIPEA) salt. Any pharmaceutical acceptable salt of Micafungin may be further prepared using a Micafungin product prepared according to the present invention. Useful pharmaceutical acceptable salts may be selected from the group consisting of the sodium salt and potassium salt.

The Micafungin prepared according to the present invention may furthermore optionally be purified using methods well known to the skilled person. According to one embodiment of the present invention, the product of step c) of the present invention is transformed to the DIPEA salt of Micafungin and thereafter transferred to a pharmaceutically acceptable salt of Micafungin, such as the sodium salt of Micafungin and further purified by chromatography Micafungin being prepared according to the present invention may be used in the manufacturing of pharmaceutical composition useful for the treatment and prevention of infectious diseases in mammals, including humans and animals. Said pharmaceutical composition may be prepared using standard techniques well known in the art. The pharmaceutical composition may also be subjected to conventional pharmaceutical operations such as sterilization.

For example, a pharmaceutical composition may be prepared in from of a dosage unit containing a given amount of purified Micafungin, alone or in combination with another active ingredient, and together with pharmaceutically acceptable excipients. The term "pharmaceutical acceptable excipient" refers to one or more formulation materials suitable for accomplishing or enhancing the delivery of Micafungin contained in the pharmaceutical composition to the patients in need thereof. A "pharmaceutical acceptable excipient" may also be represented by the presence of adjuvants, such as preservatives, stabilizers, wetting agents, emulsifiers, buffers and the like. Lactose is an example of a suitable stabilizer for Micafungin, especially in lyophilized form. The skilled person will be well aware of the various pharmaceutical excipients available for the preparation of pharmaceutical formulations comprising antifungal compounds like Micafungin. The composition according to the present invention may be prepared to enable parenteral administration, e.g. intravenous administration.

The patient in need for a composition according to the present invention may be administered a suitable dosage of Micafungin. A suitable daily dose for a human or mammal may vary widely depending on the condition of the patient and other factors. The daily dose may be determined by the skilled artisan using routine methods and which are commonly used for the treatment and prevention of infections when administering Mycamine®.

A skilled person will from the following examples acknowledge the many advantages of the present invention. The experiments and results below are furthermore to be understood to serve as non-limiting examples only.

EXAMPLE 1

Making of the Activated Micafungin Side Chain

FR-195752 (10.0 g) and HOBt (5.2 g) (comprising 12% water) was suspended in DMF (142 ml) and stirred for 5 min. EDC HCl (6.6 g) was added to the suspension. The reaction mixture was stirred for 4 h at 25° C. The reaction mixture was poured into 426 ml acetonitrile (ACN) and stirred for 18 h at 25° C. The white suspension was filtrated and dried on the filter for 2 h. The isolated yield was 12.6 g (95%) with HPLC purity: 98.0%

EXAMPLE 2

Coupling of the Activated Micafungin Side Chain to the Micafungin Peptide Core

FR-179642 (10.0 g) was suspended in dry DMF (200 ml) by stirring at 25° C. for 10 min. The mixture was cooled to 0° C. Micafungin side chain (4.50 g) and the activated acid described in example 1 were added, followed by DIPEA (2.25 ml). All material was dissolved after 5 min, and the mixture was stirred for 90 min at 0° C. A mixture of methanol (50 ml) and acetone (100 m) was added, and the temperature was raised to 10° C. The mixture was stirred at this temperature for 60 min. Ethyl acetate (1000 ml) was slowly added over 2.5 h. The resulting suspension was stirred for 15 h, and the product was collected by pressure filtration using the Aldrich 1000 ml glass pressure filter equipped with a fine coarse glass sinter filter disk. The filter cake was washed with ethyl acetate (1500 ml and dried on the filter for 15 min. Further drying in vacuum cabinet at 25° C. for 3 h afforded 12.8 g (86%) of a white solid.

EXAMPLE 3

Activating and Coupling of the Micafungin Side Chain to the Micafungin Peptide Core FR-195752 (394 mg) and HOBt hydrate (197 mg) were suspended in DMF (15 ml) at 25° C. EDC HCl (166 mg) was added, and the mixture was stirred at 25° C. for 4 h. The mixture was cooled to 0° C., and DIPEA (0.223 ml) was added followed by FR-179642 (1.00 g). The mixture was stirred for 90 min at 0° C. A mixture of methanol (2.5 ml) and acetone (5 ml) was added, and the mixture was heated to 10° C. and stirred for 60 min. Ethyl acetate (100 ml) was added over 30 min, and the resulting suspension was stirred for 16 h at 10° C. The solid product was collected filtration, washed with ethyl acetate (150 ml) and dried on the filter for 15 min. Additional drying in vacuum cabinet at 25° C. for 2 h afforded 1.47 g (98% yield) of a white solid. HPLC purity 96.6%

EXAMPLE 4

Activating and Coupling of the Micafungin Side Chain to the Micafungin Peptide Core FR-195752 (2.06 g) and Oxyma (834 mg) were suspended in DMF (60 ml) at 25° C. EDC HCl (1.07 g) was added, and the mixture was stirred at 25° C. for 2 h. The reaction mixture became a bright yellow solution. The yellow solution was cooled to 0° C., and DIPEA (1.1 ml) was added followed by FR-179642 (5.00 g). The mixture was stirred for 90 min at 0° C. A mixture of methanol (15 ml) and acetone (30 ml) was added, and the mixture was heated to 10° C. and stirred for 60 min. Ethyl acetate (300 ml) was added over 30 min, and the resulting suspension was stirred for 20 h at 10° C. The solid product was collected by filtration, washed with ethyl acetate (100 ml) and dried on the filter for 15 min. Additional drying in vacuum cabinet at 25° C. for 2 h afforded: 6.68 g (90% yield) of an off-white solid.

EXAMPLE 5

Comparison of the Chromatograms from Example 2-4

HPLC chromatograms of the crude products from Example 2-4 were analyzed by HPLC (Reverse Phase Chromatography. Table 1 shows the results from the HPLC chromatograms comparing the 3 different processes (see FIG. 4a-4c). Example 2 is the step-wise process and examples 3 and 4 are the one-pot procedures using HOBt and Oxyma as coupling additives, respectively. The Oxyma is not present in the chromatogram in the crude product. In the reaction mixture Oxyma appears at 8.5 min.

TABLE 1

HPLC chromatogram of the crude products isolated from Example 2-4.

| | RRT 0.26 FR-179642 | RRT 0.42 HOBt | RRT 0.60 Oxyma | RRT 1 Micafungin | RRT 1.31 Impurity | RRT 1.35 Impurity | RRT 1.39 Impurity |
|---|---|---|---|---|---|---|---|
| Example 2 | 0.27% | 0.59% | — | 96.67% | | 0.06% | |
| Example 3 | 0.07% | 0.72% | — | 96.62% | | 0.12% | |
| Example 4 | 0.16% | — | — | 98.00% | 0.10% | 0.14% | 0.12% |

Figure 1:
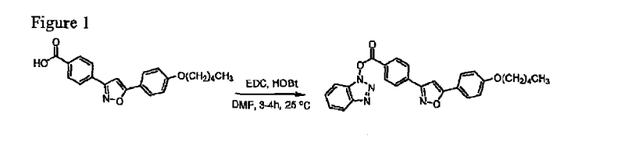
FIG. 1 is a reaction scheme illustrating the reaction as described in Example 1, i.e. the separate reaction of the Micafungin side chain and a coupling additive represented HOBt.
Figure 2:
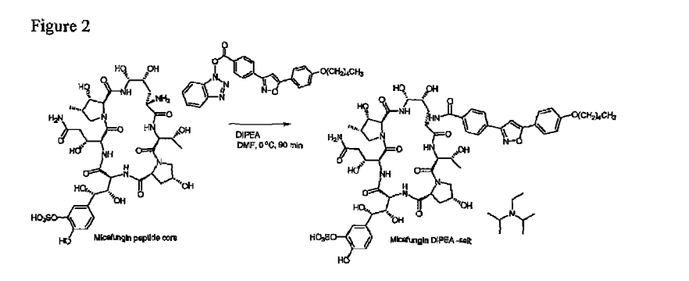
FIG. 2 is a reaction scheme illustrating the reaction as described in Example 2, i.e. the separate reaction of Micafungin peptide core and product of the reaction shown in FIG. 1.
Figure 3:
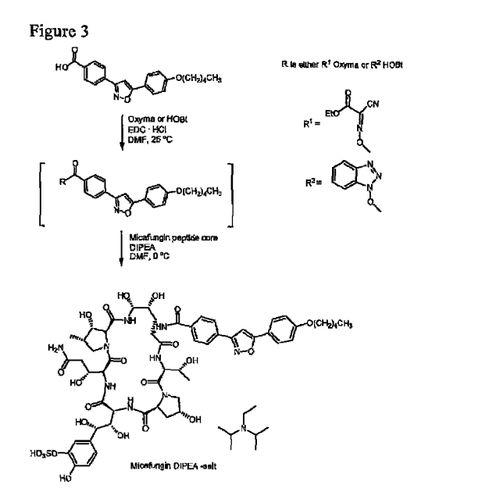
FIG. 3 is a reaction scheme illustrating the reactions as described in Example 3 and Example 4, i.e. where the activation of the Micafungin side chain and the reaction with Micafungin peptide core is performed in a one-pot process according to the present invention.
Figure 4A:
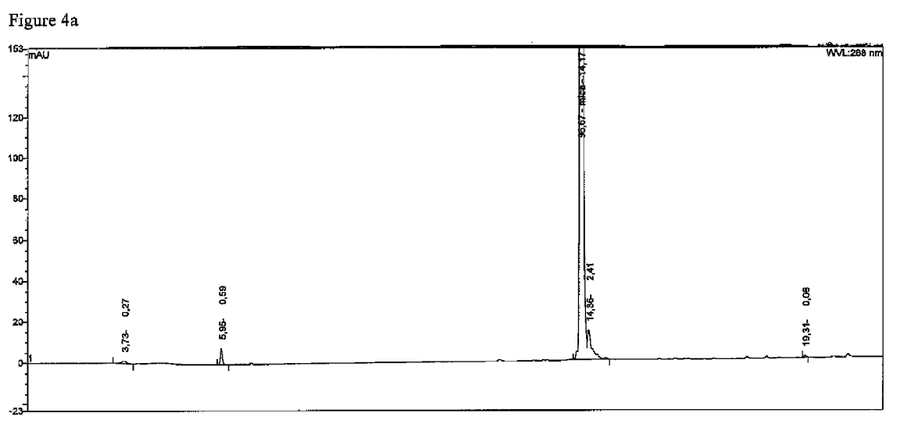
FIG. 4a represents a chromatogram of the product of the step-wise process disclosed in Example 2.
Figure 4B:
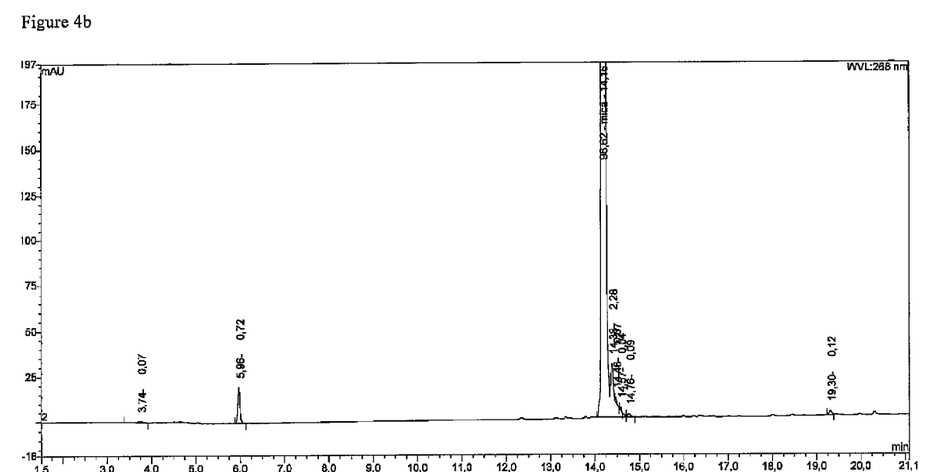
FIG. 4b represents a chromatogram of the product of the one-pot process disclosed in Example 3.
Figure 4C:
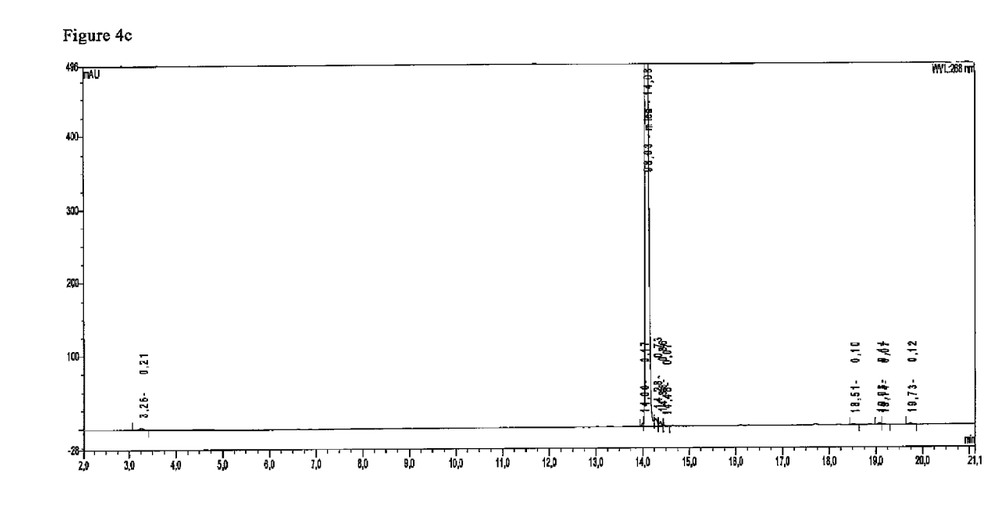
FIG. 4c represents a chromatogram of the product of the one-pot process disclosed in Example 4.

Process 3 and 4 are more effective since less solvent are being used and the reaction times are reduced since the isolation of the activated acid is circumvented. The yields by weight are significantly better in the one-pot procedures, which are 98% and 95% in examples 3 and 4 respectively, compared with only 82% in the prior art method. As seen by the examples, the one-pot method according to the present application allows production of Micafungin as pure as the step-wise prior art methods but with better yield and about the same purity of the crude product as seen in FIG. 4a-c.

The invention claimed is:

1. A one-pot process for the manufacturing of Micafungin or a salt thereof comprising the following order of steps:

a) mixing a compound of the formula (III)

(III)

or a salt thereof, and a coupling additive selected from the group consisting of hydroxybenzotriazols and ethyl-2-cyano-2-(hydroxyimino)acetate in a solvent;

b) adding an coupling reagent to the mixture obtained in step a), wherein said coupling reagent is a carbodiimide;

c) adding a base and a compound of formula (II)

(II)

or a salt thereof to the mixture obtained in step b).

2. The process of claim 1, wherein the coupling additive is 1-hydroxy-benzotriazole.

3. The process of claim 1, wherein the coupling additive is 1-hydroxy-7-azabenzotriazole.

4. The process of claim 1, wherein the coupling additive is ethyl-2-cyano(hydroxyimino)acetate.

5. The process of claim 1, wherein the coupling reagent is 1-ethyl-3-(3-dimethylaminopropyl) carbodiimide (EDC) or a salt thereof.

6. The process of claim 5, wherein the coupling reagent is the hydrochloride salt of EDC.

7. The process of claim 1, wherein the solvent used in step a) is DMF.

8. The process of claim 1, wherein the base used in step c) is DIPEA.

9. The process of claim 1, wherein the base is added to the mixture obtained in step b) before adding the compound of formula II.

10. The process of claim 1, wherein the base is added to the mixture obtained in step b) after adding the compound of formula II.

11. The process of claim 1, wherein the Micafungin salt obtained in step c) is precipitated.

12. The process of claim 11, wherein the Micafungin salt obtained in step c) is precipitated by using an antisolvent.

13. The process of claim 12, wherein the antisolvent is ethyl acetate.

14. The process of claim 11, wherein the Micafungin salt obtained in step c) is precipitated after quenching of the reaction by addition of methanol and acetone.

* * * * *